United States Patent

Viscardi et al.

[11] Patent Number: 5,925,753
[45] Date of Patent: Jul. 20, 1999

[54] PROCESS FOR THE PREPARATION OF 5H, 9BH-2A, 4A, 7, 9A-OCTAHYDRO-TETRAAZACYCLOOCTA[CD]PENTALENE

[75] Inventors: Carlo Felice Viscardi; Marina Ausonio; Massimo Gagna; Carlo Secchi, all of Milan, Italy

[73] Assignee: Dibra S.p.A., Italy

[21] Appl. No.: 09/095,017

[22] Filed: Jun. 10, 1998

[30] Foreign Application Priority Data

Jun. 11, 1997 [IT] Italy .................... MI97A1374

[51] Int. Cl.[6] .............. C07D 487/22; C07D 403/14
[52] U.S. Cl. .................................. 540/479; 540/474
[58] Field of Search ...................... 540/479, 474

[56] References Cited

U.S. PATENT DOCUMENTS 4,130,715  12/1978  Atkins ...................... 548/324

OTHER PUBLICATIONS

Weisman et al., Tetrahedron Letters., vol. 21, 1980 pp. 3635–3638.
Atkins., J. Amer. Chem. Soc., 102, 1980 p. 6364.

Primary Examiner—Richard L. Raymond
Assistant Examiner—Pavanaram K Sripada
Attorney, Agent, or Firm—Nixon & Vanderhye

[57] ABSTRACT

A process for the preparation of 5H,9bH-2a,4a,7,9a-octahydrotetraazacycloocta[cd]pentalene of formula (I)

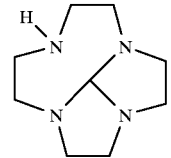

(I)

which comprises the reaction of 1,4,7,10-tetraazacyclododecane with triethyl orthoformate in the absence of solvent and in the presence of an acid catalyst.

13 Claims, No Drawings

PROCESS FOR THE PREPARATION OF 5H, 9BH-2A, 4A, 7, 9A-OCTAHYDRO-TETRAAZACYCLOOCTA[CD]PENTALENE 5H,9bH-2a,4a,7,9a-Octahydro-tetraazacycloocta[cd]-pentalene (CAS RN 67705-42-4) of formula (I), described below, is an intermediate for the preparation of 1,4,7,10-tetraazacyclododecane derivatives wherein three nitrogen atoms are substituted with the same functional group, for example a carboxymethyl group, whereas the fourth nitrogen atom is substituted with a group different from the previous one.

It is particularly important, for example, the synthesis of 1,4,7,10-tetraazacyclododecane-1,4,7-triacetic acid (more commonly known as DO3A), of formula (II), which was described in various places, first in EP 292,689 and in EP 23,2751 and subsequently in a paper (Dischino et al., Inorg. Chem., 1991, 30, 1265), wherein the synthesis according to scheme 1 is described in detail.

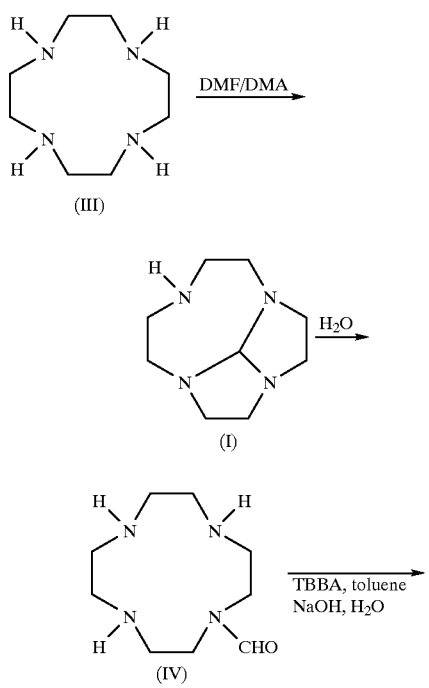

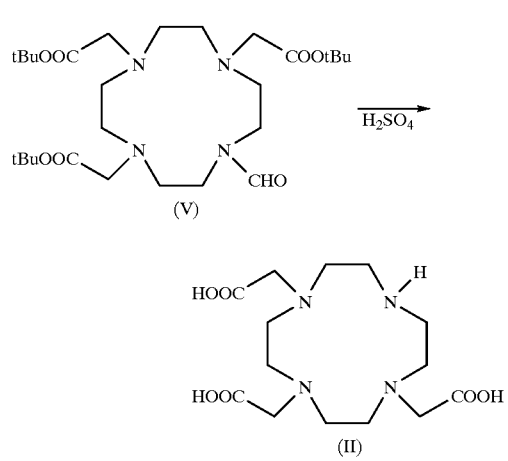

The step from the commercially available starting product 1,4,7,10-tetraazacyclododecane (III), to compound of formula (I) is effected according to the conventional method described in U.S. Pat. No. 4,085,106, followed by formation of 1-formyl-1,4,7,10-tetraazacyclododecane of formula (IV) in water-alcohol medium.

This intermediate is subsequently tricarboxymethylated with tert-butyl bromoacetate (TBBA) in dimethylformamide, then treated with a toluene-sodium hydroxide diphasic mixture to give the compound of formula (V), 10-formyl-1,4,7,10-tetraazacyclododecane-1,4,7-triacetic acid, tris(1,1-dimethylethyl) ester, which is then hydrolysed to compound of formula (II) in acidic solution.

Macrocyclic derivatives of this type are intermediates for the preparation of gadolinium complexes which can be used as contrast agents for magnetic resonance (MRI), such as Gadoteridol of formula (VI), gadolinium complex of 10-(2-hydroxypropyl)-1,4,7,10-tetraazacyclododecane-1,4,7-triacetic acid, or Gadobutrol of formula (VII), gadolinium complex of [10-[2,3-dihydroxy-1-(hydroxymethyl)propyl]-1,4,7,10-tetraazacyclododecane-1,4,7-triacetic acid.

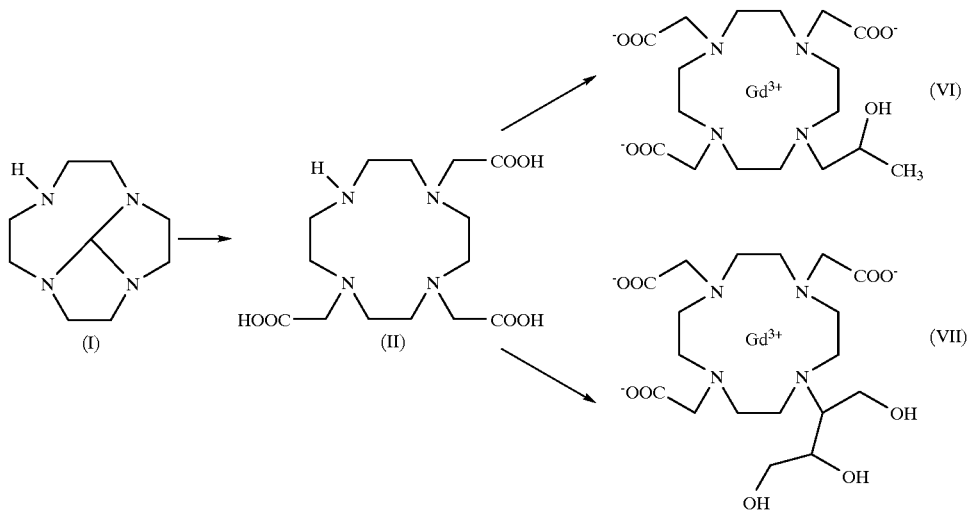

The preparation of compound (I) at high purity level in easily reproducible conditions is an essential requirement for the preparation of these important diagnostic agents an industrial scale.

Compound (I) and its preparation were described first in U.S. Pat. No. 4,130,715 or in U.S. Pat. No. 4,085,106, such a process being used also in the other references wherein this type of intermediate is necessary.

The described procedures are based on the use of dialkylformamides-dialkylacetals: for example, J. Atkins (cited patents) discloses the synthesis of compound (I) in an aromatic solvent (benzene), by reacting 1,4,7,10-tetraazacyclododecane and N,N-dimethylformamide-dimethylacetal (usually in equimolar amounts) without catalyst.

Aliphatic and cycloaliphatic hydrocarbons, chlorinated hydrocarbons, dialkyl ethers and alkylnitriles can be used as alternative solvents to the aromatic ones.

Atkins himself (J. Am. Chem. Soc. 1980, 102, 6364–6365) makes also reference to the possibility of operating in the absence of solvents.

Although these conditions provide compound (I) in good yields, their application on industrial scale is difficult due to the extreme reactivity of dialkylformamide-dialkylacetal towards such nucleophiles as water and the compound (I) itself.

In order to avoid an excessive formation of by-products, which involves a decrease in the yield and a worsening in the quality of compound (I), it is necessary: a) to operate in anhydrous conditions and b) to add dialkylformamide-dialkylacetal in amounts which are equimolar to 1,4,7,10-tetraazacyclododecane or, anyway, such as to cause a complete conversion of the latter.

The presence of water in the reaction can involve, on one hand, the destruction of dialkylformamide-dialkylacetal and, on the other hand, the hydrolysis of compound (I) to 1-formyl-1,4,7,10-tetraazacyclododecane, which can in turn react with dialkylformamide-dialkylacetal and produce further by-products.

Commercial 1,4,7,10-tetraazacyclododecane usually contains water in minimum percentages, which is however sufficient to hydrolyse an unnegligible part of the reactive or of the compound (I) itself: it is therefore necessary for the reaction environment to be dry before the addition of dimethylformamide-dialkylacetal. If the solvent used is an aromatic solvent, the reaction solution is particularly troublesome to dry: for example, the distillation of the water-toluene azeotrope involves high consumption of the organic solvent and it requires rather long times, thus affecting productivity.

On the other hand, the addition of dialkylformamide-dialkylacetal is critical, in that an excess thereof causes the rapid formation of by-products, whereas a lack thereof means that some residual 1,4,7,10-tetraazacyclododecane is still present, to the detriment of the progress of the synthesis for the preparation of the above cited macrocyclic derivatives. The control of the reaction stoichiometry is quite critical and difficult, considering also that dimethylformamide-dimethylacetal assay tends to decrease with time. On an industrial scale, therefore, successful results can be obtained only when the progress of the reaction is checked through a number of process controls: for example, 1,4,7,10-tetrazazacyclododecane actually disappears generally only after gradual additions of dialkylformamide-dialkylacetal, determined by gas-chromatographic controls.

A further complication deriving from the use of a dialkylformamide-dialkylacetal on an industrial scale is that the plant must be equipped with a suitable gas scrubber, if the above cited dialkylformamide-dialkylacetal reagent/ is commercially available, such as N,N-dimethylformamide-dimethylacetal or N,N-dimethylformamide-diethylacetal. The reaction carried out with these reagents causes, in fact, the formation of gaseous dimethylamine, which has to be suitably removed, for example by means of a sulfuric acid absorber.

Furthermore, the reaction is usually carried out in the presence of rather high amounts of an aromatic solvent, thereby affecting productivity and costs in terms of purchase, recovery and disposal of the used solvent. As a matter of fact, the mass reaction described by Atkins is of little applicability on an industrial scale as the first reagent is highly reactive and highly toxic and the second one is a solid, thus causing problems in terms of operation and thermal control.

Finally, the high cost of dimethylformamide dimethylacetal makes the process less attractive.

The main alternative to dialkylformamides-dialkylacetals consists in the use of trialkyl orthoformates, which have, according to literature (Weisman, Tetrahedron Letters, 21, 3635–3638, 1980), a lower reactivity than the above mentioned dialkylformamides-dialkylacetals, so that the reaction cannot be completed, in spite of the addition of an acid catalyst.

The low yields reported by Weisman in the case of reactions carried out in aromatic solvents do not support the applicability of the procedure on an industrial scale.

On the other hand, the examples of acid-catalyzed mass reactions between polyamines and triethyl orthoformate (Stetter, Chem. Ber. 106, 2523–2529, 1973) are characterized as well by yields too low for any industrial applications in the synthesis of the compound (I), which would be extremely uneconomic.

It has now surprisingly been found, and this is the object of the present invention, that, under suitable conditions, 1,4,7,10-tetraazacyclododecane can be transformed into compound (I) in high yields, using triethyl orthoformate, in the absence of solvent and in the presence of an acid catalyst at high temperature.

Conditions excluding oxygen and light from the reaction environment are further preferred, oxygen being excluded, for example, making use of the usual nitrogen blanket techniques.

Triethyl orthoformate can be added in amounts ranging from 105% to 200% on the stoichiometric value.

The reaction temperature can range from 110 to 150° C. and the reaction time from 4 to 24 h.

The catalyst is a carboxylic acid having at least 3 carbon atoms, $C_3$–$C_{18}$, preferably selected from the group consisting of propionic, butyric and pivalic acids, and it is added in amounts ranging between 4 and 42 g/kg substrate.

Triethyl orthoformate is a cheaper product than N,N-dimethylformamide-dimethylacetal, produces no harmful, non-condensable gaseous by-products, only ethanol, which can be advantageously recovered for the preparation of triethyl orthoformate or for other synthetic purposes.

Moreover, triethyl orthoformate is less reactive than N,N-dimethylformamide-dimethylacetal, which makes it possible to carry out the additions of the reagents and the reaction itself in totally safe conditions even on a large scale; it allows one to better monitor the progress of the reaction on the basis of such operative parameters as time and temperature, without checking the progress by gas chromatography, and makes the addition of the reactive less critical, in that it can be added from the very beginning without causing the formation of undesired by-products: all that rendering the process suitable for the production of compound (I) in easily reproducible conditions.

As in the case of N,N-dimethylformamide-dimethylacetal, water contained in commercial 1,4,7,10-tetraazacyclododecane has to be removed: water removal can easily be performed either by melting 1,4,7,10-tetraazacyclododecane in nitrogen flux, or by addition of a suitable solvent and subsequent distillation of the solvent to a residue of dry melt 1,4,7,10-tetraazacyclododecane at a temperature higher than 110° C.

Ethyl orthoformate and the acid catalyst can be added directly to this residue without any thermal control or safety problems, in that orthoformate is poorly reactive and the reaction is not exothermic.

The drying solvent can be selected from straight or branched ($C_4$–$C_6$) alcohols, preferably from the group consisting of 1-butanol, 2-butanol, amyl alcohol, and isoamyl alcohol.

The reaction involves evolution of ethanol: a first amount of the evolved ethanol remains in the reaction mixture, until it reaches such a concentration that the vapor pressure of the reaction mixture reaches the atmospheric value. From this point on, the evolved ethanol distils from the reaction mixture together with a small amount of orthoformate. To avoid losses of orthoformate, the evolved vapor can easily be rectified with a small rectification column: the distillate from the head of the column is substantially pure ethanol, whereas the liquid from the bottom, which is enriched in orthoformate, is recycled to the reactor.

In pre-set operative conditions, the measurement of the weight or of the volume of the evolved ethanol is a convenient, precise index of the progress of the reaction.

When the reaction is completed, depending on the synthetic purposes, compound (I) can be used as such or it can be purified by fractional distillation. In both cases, the yield in compound (I) is extremely high (typically 95–98% for crude compound (I) and higher than 90% for purified compound (I)).

A further object of the present is the process for the preparation of compound (II), 1,4,7,10-tetraazacyclododecane-1,4,7-triacetic acid, comprising the following steps:

a) preparation of 5H,9bH-2a,4a,7,9a-octahydro-tetraazacyclooctat[cd]pentalene starting from 1,4,7,10-tetraazacyclododecane according to the method of the invention, which compound, without being isolated, is carboxymethylated and subsequently hydrolysed according to known methods to give the desired product.

The following examples illustrate the best experimental conditions to carry out the process of the invention.

The following gas-chromatographic method was used to control the progress of the reactions:

Instrumentation: gas-chromatographic unit Hewlett-Packard series 5890 II Plus equipped with autosampler series 7673 and unit HP-3365

Column: 25 m fused silica capillary, int. diam. 0.32 mm, stationary phase CP Sil 19CB, film thickness 0.2 $\mu$m (Chrompack art.7742)

Oven temp. program: first isotherm at 120° C. for 5 min; ramp 15° C./min; final isotherm at 260° C. for 2 min Injected volume: 1 $\mu$L Detector: FID; temperature 275° C.

Experimental Section

EXAMPLE 1

Preparation of Compound (I) by Reaction Between 1,4,7,10-tetraazacyclododecane and Triethyl Orthoformate in the Presence of Propionic Acid A glass reactor fitted with random packing column, distillation head and condenser, shielded from light with an aluminum foil, is loaded with 71.4 g (0.414 mol) of 1,4,7,10-tetraazacyclododecane and 71.4 g of n-butanol. The mixture is heated to 80° C. until complete dissolution and the solution is dried by distilling the n-butanol-water azeotrope (14.4 g) at reduced pressure, then the residual n-butanol is distilled off until bottom temperature reaches 120° C. and residual pressure reaches 20 mbar. After restoring the atmospheric pressure with nitrogen, 73.5 g (0.498 mol) of triethyl orthoformate and 0.6 g of propionic acid are added. The mixture is heated for 7 h at 135° C. while condensing the evolved ethanol and recovering it separately. The triethyl orthoformate excess is distilled off at reduced pressure to obtain 76.0 g of the desired compound (GC assay: 95% area).

Distillation at reduced pressure (7 mbar) at 128° C. gives 68.8 g (0.377 mol) of purified 5H,9bH-2a,4a,7,9a-octahydro-tetraazacycloocta[cd]pentalene (GC essay: 99% area).

Overall yield: 91%

The $^1$H-NMR, $^{13}$C-NMR, IR and MS spectra are consistent with the indicated structure.

EXAMPLE 2

Preparation of the Compound (I) by Reaction Between 1,4,7,10-tetraazacyclododecane and Triethyl Orthoformate in the Presence of Pivalic Acid.

A glass reactor fitted with random packing column, distillation head and condenser, blanketed with nitrogen under a 1 mbar gauge. pressure and shielded from light with an aluminum foil, is loaded with 102.6 g (0.593 mol) of 1,4,7,10-tetraazacyclododecane, containing 0.5% w/w of water, and the compound is melted at 140° C. under mild nitrogen stream. White crystals consisting of the sublimated substrate form in the column. After cooling to 130° C., 123 g (0.829 mol) of triethyl orthoformate and then 1 g of pivalic acid are added. After heating at 140° C. for 5 h, until recovering an ethanol amount of 90% on the stoichiometric, the triethyl orthoformate excess is distilled off under vacuum, to obtain 108 g of the desired compound as a viscous yellow oil (GC assay: 96% area).

Yield: 96%

The $^1$H-NMR, $^{13}$C-NMR, IR and MS spectra are consistent with the indicated structure.

EXAMPLE 3

Repetition of the Preparation of Example 2 in the Presence of Atmospheric Oxygen and Light.

The procedure of the example 2 is repeated in a reactor blanketed with dry air without shielding with aluminum foil. The same amount of product is obtained, but its dark and with a markedly lower g.c. assay (89%).

EXAMPLE 4

Preparation of Compound (I) by Reaction Between 1,4,7,10-tetraazacyclododecane and Triethyl Orthoformate in the Presence of Propionic Acid

A glass reactor fitted with a random packing column, distillation head and condenser and shielded from light with an aluminum foil is loaded with 110 g (0.634 mol) of 1,4,7,10-tetraazacyclododecane, containing 0.7% w/w of water, and the compound is melted at 140° C. under mild nitrogen stream. After cooling to 115° C., 113 g (0.761 mol) of triethyl orthoformate and 1.65 g of propionic acid are added. The mixture is reacted for 20 h at 115° C., while distilling off ethanol. Finally the triethyl orthoformate excess is distilled under vacuum, to obtain 115 g of the desired product (GC assay: 95% area).

Yield: 94%

The $^1$H-NMR, $^{13}$C-NMR, IR and Ms spectra are consistent with the indicated structure.

EXAMPLE 5

Preparation of Compound (I) and Immediate Conversion to 1,4,7,10-tetraazacyclododecane-1,4, 7-triacetic Acid (II)

A) Preparation of an Aqueous Solution of Compound (II) as Trisodium Salt 110 g (0.634 mol) of 1,4,7,10-tetraazacyclododecane containing 0.7% w/w of water are dissolved in 110 g of amyl alcohol. The water-amyl alcohol azeotrope and the amyl alcohol excess are distilled off under vacuum, in succession, then 113 g (0.761 mol) of triethyl orthoformate and 1.2 g of propionic acid are added, in nitrogen atmosphere. The mixture is heated for 8 h at 135° C., while distilling the formed ethanol, then the reaction mixture is cooled to 35° C., to obtain the crude compound (I) as fluid oil which is added to a solution prepared dissolving 274 g (1.972 mol) bromoacetic acid and 263 g 30% w/w NaOH in 370 g water. During the addition of the crude compound (I), pH is kept at 10 by addition of NaOH; at the end of the addition, pH is adjusted to 11.3, again by addition of 30% w/w NaOH, and the mixture is reacted for 24 h at 30° C.

360 g of 30% w/w NaOH are then added, and the solution is heated at 75° C. for 9 h. An aqueous solution containing 204 g (0.589 mol) of 1,4,7,10-tetraazacyclododecane-1,4,7-triacetic acid (content determined by HPLC), as trisodium salt, is obtained.

Yield: 93%

B) Recovery of compound (II) as sulfate

The solution from step A) is acidified with 192 g of 40% $H_2SO_4$ and added with acetone to precipitate 70.2 g of the desired compound (0.158 mol).

Yield: 81%

The $^1$H-NMR, $^{13}$C-NMR, IR and MS spectra are consistent with the indicated structure.

C) Free acid from the salt obtained at step B)

The salt obtained at step B) is loaded onto a PVP resin (according to the procedure described in Dischino et al., Inorg. Chem., 1991, 30. 1265). 49.25 g of the compound (II) (0.142 mol) are obtained.

Yield: 90%

The $^1$H-NMR, $^{13}$C-NMR, IR and MS spectra are consistent with the indicated structure.

EXAMPLE 6

Preparation of Compound (I) and Immediate Conversion to 1,4,7,10-tetraazacyclododecane-1,4, 7-triacetic Acid (II) Usable for the Synthesis of Gadoteridol

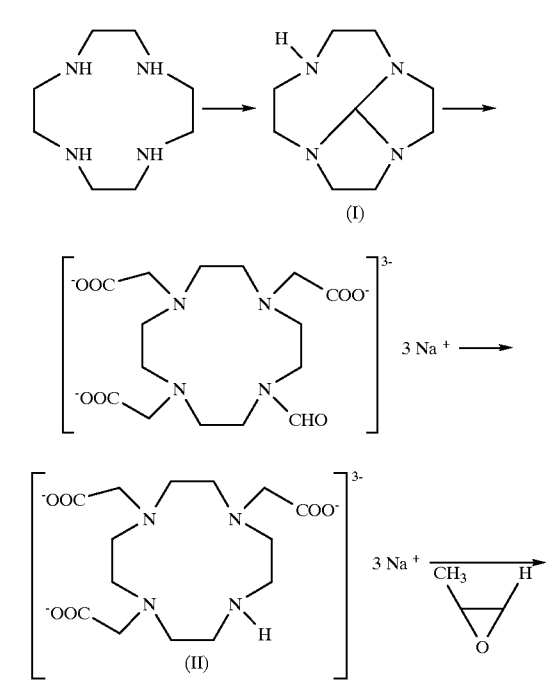

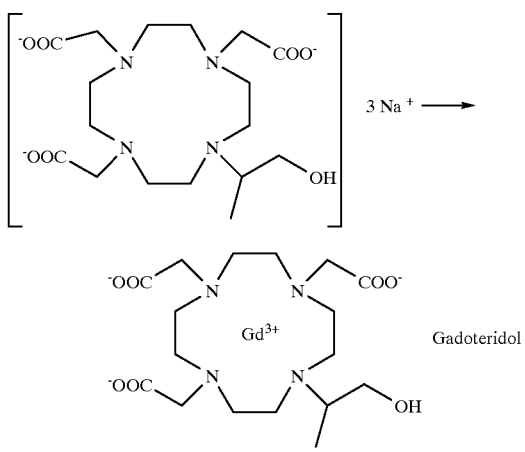

Gadoteridol

A) Preparation of Compound (I)

23.8 kg (0.138 kmol) of 1,4,7,10-tetraazacyclododecane containing 0.7% w/w of water are dissolved in 23.8 kg of amyl alcohol. The water-amyl alcohol to pH 1.7 with conc. HCl, and pH is controlled at this value for 2 h. After that, the solution is heated at 50° C., pH is adjusted to 7 with sodium hydroxide, and the solution is maintained at these conditions for 1 h.

E) Prepurification of the Gadoteridol Crude Solution

The Gadoteridol crude solution from the previous step is cooled and transferred through an in line filter and a column packed with 150 L of R&H Amberlite XAD 1600 resin to a nanofiltration unit fitted with Desal DK4040F elements. When the reactor is empty, the reactor, the in line filter and the column are washed three times with 300 L of deionized water. The resulting washing solution is combined with the product solution in the nanofiltration unit, where the product is concentrated and partially desalted at 32 bar and 25° C.

250 L of crude Gadoteridol solution with a conductivity of 2.9 mS/cm are obtained finally.

F) Final Desalting

The Gadoteridol solution is then fed at 200 L/h to a series of 4 ion exchanger beds, the first (C1) consisting of 120 L of strongly basic anion exchanger Relite 3ASfb in the hydrogen carbonate form, the second (C2) consisting of 100 L of weakly acidic cation exchanger Relite CC in the $H^+$ form, the third (C3) consisting of 20 L of Relite 3ASfb in the $OH^-$ form and the fourth (C4) consisting of 20 L of Relite CC resin in the $H^+$ form. All the columns are vented to the atmosphere and the liquid from the second column is passed through a gas separation tank, connected with a vacuum pump, to remove the evolved $CO_2$ from the solution. The outlet from the fourth column is fitted azeotrope and the amyl alcohol excess are distilled at reduced pressure, in succession, then 24.5 kg (0.166 kmol) of triethyl orthoformate and 355 g of propionic acid are added in nitrogen atmosphere. The mixture is heated for 11 h at 125° C., while distilling the formed ethanol, then the reaction mixture is cooled to 35° C., to obtain compound (I) as a fluid oil.

B) Preparation of 10-formyl-1,4,7,10-tetraazacyclododecane-1,4,7-triacetic Acid Sodium Salt Compound (I) obtained at step A) is added to a solution prepared dissolving 81.5 kg (0.469 kmol) of bromoacetic acid and about 62.6 kg of 30% w/w NaOH in 100 kg of water to pH 5. During the addition of the crude compound (I), pH is kept at 11 by addition of NaOH; at the end of the addition, pH is adjusted to 11.1, again by addition of 30% w/w NaOH, and the mixture is reacted for 24 h at 35° C.

C) Preparation of 1,4,7,10-tetraazacyclododecane-1,4,7-triacetic Acid Sodium Salt The mixture from step B) is then added with 77.3 kg of 30% w/w NaOH and heated to 70° C. for 9 h. The resulting aqueous solution contains 0.131 kmol of the desired compound (content determined by HPLC), as a trisodium salt.

D) Synthesis of Gadoteridol pH is adjusted to 12.3 with conc. HCl, 15.2 kg (0.262 kmol) propylene oxide are added, and the mixture is reacted for 4 h at 40° C. After that, the solution is heated to 50° C. and added with 120 kg of an aqueous solution containing 0.135 kmol gadolinium trichloride. After 1 h, the mixture is cooled to 17° C. and acidified with a density transmitter to detect the product in the eluate. The first 180 L of eluate are discarded; the eluate is then collected in a product-rich fraction. When all the crude Gadoteridol solution has been loaded onto the ion exchange unit, the product is eluted with 600 L of deionized water, the eluate is then combined with the product-rich fraction, which is colourless and substantially free from ionic impurities (conductivity 2.2 $\mu$S/cm).

The yield of the final desalting, determined by HPLC, is 98%.

G) Recovery of the Product (Gadoteridol)

The product-rich fraction is then thermally concentrated to a viscous residue, which is added with 350 kg of isopropanol at 79° C.

The resulting suspension is refluxed for 1 h, then cooled, centrifuged and dried at reduced pressure, to obtain 68.2 kg of Gadoteridol containing 10% of hydration water (0.111 kmol), HPLC assay 98.5% (s.a.).

Overall Yield: 80.7%

The $^1$H-NMR, IR and MS spectra are consistent with the indicated structure.

We claim:

1. A process for the preparation of 5H,9bH-2a,4a,7,9a-octahydrotetraazacycloocta[cd]pentalene which comprises reaction of 1,4,7,10-tetraazacyclododecane with triethyl orthoformate in the absence of solvent and in the presence of an acid catalyst.

2. A process as claimed in claim 1, wherein oxygen and light are excluded from the reaction environment.

3. A process as claimed in claim 2, wherein oxygen is excluded by means of nitrogen blanket.

4. A process according to claim 1, wherein triethyl orthoformate is added in amounts ranging between 105% and 200% of the stoichiometric value.

5. A process according to claim 1, wherein temperature ranges from 110° C. to 150° C. and the reaction time between 4 and 24 hours.

6. A process according to claim 1, wherein the acid catalyst is a carboxylic acid having 3 to 18 carbon atoms and is added in amounts ranging between 4 and 42 g/kg substrate.

7. A process as claimed in claim 6, wherein said carboxylic acid is selected from the group consisting of propionic, butyric and pivalic acids.

8. A process according to claim 1, wherein 1,4,7,10-tetraazacyclododecane is dried by melting in nitrogen flux atmosphere.

9. A process according to claim 1, wherein 1,4,7,10-tetraazacyclododecane is dried by addition of a suitable solvent and subsequent distillation of the solvent.

10. A process as claimed in claim 9, wherein said solvent is a straight or branched $C_4$–$C_6$ alcohol.

11. A process as claimed in claim 10, wherein said alcohol is selected from the group consisting of 1-butanol, 2-butanol, amyl alcohol, and isomayl alcohol.

12. A process according to claim 1, wherein the vapor evolved during the reaction is rectified and the liquid from the bottom of the column is recycled to the reactor.

13. A process according to claim 1, wherein the progress of the reaction is monitored by measuring the amount of evolved ethanol.

* * * * *